(12) United States Patent
Kulkarni et al.

(10) Patent No.: US 9,173,845 B2
(45) Date of Patent: Nov. 3, 2015

(54) CONTROLLED RELEASE PHARMACEUTICAL COMPOSITIONS OF MILNACIPRAN

(75) Inventors: Shirish Kumar Kulkarni, Pune (IN);
Rajesh Kulkani, Pune (IN);
Pandharinath Jadhav, Pune (IN);
Ashish Tiwari, Pune (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 180 days.

(21) Appl. No.: 13/388,838

(22) PCT Filed: Aug. 4, 2010

(86) PCT No.: PCT/IN2010/000520
§ 371 (c)(1),
(2), (4) Date: Feb. 3, 2012

(87) PCT Pub. No.: WO2011/016057
PCT Pub. Date: Feb. 10, 2011

(65) Prior Publication Data
US 2012/0128772 A1 May 24, 2012

(30) Foreign Application Priority Data
Aug. 5, 2009 (IN) .......................... 1041/KOL/2009

(51) Int. Cl.
*A61K 9/24* (2006.01)
*A61K 9/20* (2006.01)
*A61K 31/165* (2006.01)

(52) U.S. Cl.
CPC .............. *A61K 9/2027* (2013.01); *A61K 9/209* (2013.01); *A61K 9/2013* (2013.01); *A61K 9/2054* (2013.01); *A61K 9/2086* (2013.01); *A61K 9/2095* (2013.01); *A61K 31/165* (2013.01)

(58) Field of Classification Search
CPC ......... A61K 9/20; A61K 9/2086; A61K 9/28; A61K 9/209; A61K 9/2095
USPC ................................................ 424/465–489
See application file for complete search history.

(56) References Cited

U.S. PATENT DOCUMENTS

| | | | |
|---|---|---|---|
| 4,478,836 A | 10/1984 | Mouzin et al. | |
| 6,033,685 A * | 3/2000 | Qiu et al. | 424/464 |
| 6,602,911 B2 | 8/2003 | Kranzler et al. | |
| 6,699,506 B1 | 3/2004 | Paillard et al. | |
| 2003/0203055 A1 * | 10/2003 | Rao et al. | 424/738 |
| 2004/0132826 A1 | 7/2004 | Hirsh et al. | |
| 2006/0024366 A1 | 2/2006 | Hirsh et al. | |
| 2006/0063810 A1 * | 3/2006 | Vergez et al. | 514/321 |
| 2009/0018203 A1 * | 1/2009 | Hirsh et al. | 514/619 |

FOREIGN PATENT DOCUMENTS

| | | |
|---|---|---|
| WO | WO 2006/088305 A1 | 8/2006 |
| WO | WO 2006/132307 A1 | 12/2006 |

OTHER PUBLICATIONS

Puech et al., "Milnacipran, a new serotonin and noradrenaline reuptake inhibitor: an overview of its antidepressant activity and clinical tolerability," *International Clinical Psychopharmacology* (1997) 12: 99-108.
International Search Report (Form PCT/ISA/210) for corresponding International Application No. PCT/IN2010/000520.
Written Opinion (Form PCT/ISA/237) for corresponding International Application No. PCT/IN2010/000520.

* cited by examiner

*Primary Examiner* — Michael G Hartley
*Assistant Examiner* — Micah-Paul Young
(74) *Attorney, Agent, or Firm* — Merchant & Gould P.C.

(57) ABSTRACT

A controlled release pharmaceutical composition comprising Milnacipran or pharmaceutically acceptable salts thereof and hydrophobic release controlling agent. The composition releases 90% of the total amount of Milnacipran or pharmaceutically acceptable salts thereof between 8 to 20 hours when dissolution is carried out in 900 ml 0.1N HCl, USP apparatus Type I (Basket) at 100 rpm for 2 hrs, followed by 900 ml Phosphate buffer pH 6.8 USP apparatus Type I (Basket) at 100 rpm. A process of preparing a controlled release pharmaceutical composition comprises: a) preparing a first layer comprising i) melting hydrophobic release controlling agent and Milnacipran or pharmaceutically acceptable salts thereof in it ii) cooling followed by sieving the melted mass to obtain granules and iii) lubricating the granules; and b) preparing a second layer comprising granules which comprises hydrophobic release controlling agent and optionally Milnacipran or pharmaceutically acceptable salts thereof.

12 Claims, 4 Drawing Sheets ific equipments or techniques.
CONTROLLED RELEASE PHARMACEUTICAL COMPOSITIONS OF MILNACIPRAN This application is a National Stage Application of PCT/IN2010/000520, filed 4 Aug. 2010, which claims benefit of Serial No. 1041/KOL/2009, filed 5 Aug. 2009 in India and which applications are incorporated herein by reference. To the extent appropriate, a claim of priority is made to each of the above disclosed applications.

FIELD OF THE INVENTION

The present invention relates to novel controlled release pharmaceutical compositions comprising Milnacipran or pharmaceutically acceptable salts thereof.

BACKGROUND OF THE INVENTION

Milnacipran (cis-2-amino methyl-N,N-diethyl-1-phenyl cyclopropane carboxamide) is a psychoactive drug, which is a selective norepinephrine and serotonin reuptake inhibitor. It is used for the treatment of clinical depression and chronic pain especially fibromyalgia.

Milnacipran was first disclosed in U.S. Pat. No. 4,478,836. Milnacipran is currently available as Savella® immediate release tablets in USA and is used for the management of fibromyalgia.

Milnacipran has demonstrated numerous adverse reactions in human clinical trials with tolerability decreasing with increasing dose (Puech A. et al., 1997, Int. Clin. Psychopharm, 12:99-108). Milnacipran may induce a locally mediated nausea via gastric irritation and the rapid onset of nausea was observed even prior to achieving peak plasma levels. An immediate release formulation of Milnacipran may not be suitable for a once-daily dosing regimen for treatment of depression and other related diseases due to Milnacipran's relatively short, half-life, which is 8 hours approximately.

Moreover, the currently available immediate release formulation of Milnacipran is not ideal for the treatment of health conditions that require Milnacipran doses equal or above 100 mg/day given either as once a day or twice a day due to the high incidence of treatment-emergent side effects that lead to poor patient tolerance. Higher doses are required in the treatment of severe depression and other associated disorders. Milnacipran dosing regime of 100-250 mg daily was recently reported for the treatment of fibromyalgia (U.S. Pat. No. 6,602,911). It would be very difficult to reach the upper limits of the dose range using the currently available formulation due to the dose related treatment, emergent side effects and the need to titrate over a long period to reach the required dose.

Various approaches have been tried to develop controlled release pharmaceutical compositions of Milnacipran in order to lower the incidence and intensity of side effects, especially for higher dosages, and lower or reduce the frequency of dosing.

U.S. Pat. No. 6,699,506 discloses a pharmaceutical composition with prolonged release, for oral administration of a single daily dose of 60 to 140 mg of Milnacipran, having a multi-particulate form containing a plurality of microgranules each comprising an active microsphere containing a saccharose and/or starch nucleus of a size between 200 and 2000 µm and containing 150 to 1000 µm of Milnacipran and a binding agent, each microgranule being coated with a film having a base of at least one polymer insoluble in water but permeable to physiological liquids.

WO 2006/132307 provides a stabilized Milnacipran-containing composition in which Milnacipran or a salt thereof is allowed to exist in a porous carrier, packing a powder containing Milnacipran or a salt thereof in an HPMC capsule, or combining an additive which does not cause an interaction with Milnacipran with time.

WO 2006/088305 discloses a gastric-retentive controlled release mono-matrix tablet composition, comprising: a) at least one pharmacologically active substance; b) hydrogel-forming materials consisting of polyethylene oxide and at least one component selected from poloxamers and colloidal silica; and c) a carbon dioxide-generating material. The composition of the present invention floats in gastric juice and can continuously release the active substance in the stomach at a constant rate for at least 2 hours.

US 2004/0132826 and US 2006/0024366 provide an extended release dosage unit of Milnacipran (optionally containing the immediate release portion) coated with delayed release coating. The Milnacipran composition, when administered orally, first passes through the stomach releasing from zero to less than 10% of the total Milnacipran dose and then enters the intestines where drug is released slowly over an extended period of time.

Although above mentioned patents and patent applications provide controlled release dosage forms, but production of dosage forms of these references is lengthy, expensive process or requires specialized equipments or techniques.

There exists a need to develop a novel controlled release pharmaceutical composition comprising Milnacipran or pharmaceutically acceptable salts thereof, which offers advantages like simple manufacturing process, compact dosage form, use of conventional manufacturing equipment, high throughput, easy scale-up, economic, etc.

Additionally there is a need to provide a controlled release pharmaceutical composition comprising Milnacipran or pharmaceutically acceptable salts thereof, wherein composition provides complete dissolution between 8 to 20 hrs or the pharmaceutical composition of the present invention can be suitably designed to provide controlled release compositions that control release over prolonged periods of time, at least for 12 hours after oral administration. Thus the present invention provides a novel controlled release pharmaceutical composition comprising Milnacipran or pharmaceutically acceptable salts thereof, to control release over prolonged periods of time.

Object of the Invention

Therefore, as a first object, the present invention provides controlled release pharmaceutical compositions comprising Milnacipran or pharmaceutically acceptable salts thereof and hydrophobic release controlling agent.

Yet another object of the present invention is to provide controlled release pharmaceutical compositions comprising Milnacipran or pharmaceutically acceptable salts thereof and hydrophobic release-controlling agent adapted to release the active over a predetermined time period, at least for 12-14 hours. A suitable dissolution test is where the measurement is carried out in a type II dissolution (50 rpm) apparatus or type I dissolution (100 rpm) apparatus according to U.S. pharmacopoeia in aqueous buffer at 37° C. or variations on this as well known to one who is skilled in the art.

The present invention proposes controlled release pharmaceutical compositions of Milnacipran or pharmaceutically acceptable salts thereof wherein the complete dissolution time that is the time for release of 90% of the total amount of the drug is between 8 to 20 hours, preferably between 8 to 12 hours.

Yet another object of the invention proposes controlled release pharmaceutical compositions of Milnacipran or pharmaceutically acceptable salts thereof wherein pharmaceutical composition releases at least 90% of the active in 12 hrs.

Yet another object of the invention proposes controlled release pharmaceutical compositions of Milnacipran or pharmaceutically acceptable salts thereof, which exhibits a mean $C_{max}$ in the range from 50 ng/ml to 2000 ng/ml in fasted conditions.

Yet another object of the invention provides once daily controlled release pharmaceutical composition comprising Milnacipran or pharmaceutically acceptable salts thereof and hydrophobic release controlling agent for the management of fibromyalgia.

Yet another object of the invention provides a once daily controlled-release pharmaceutical composition comprising Milnacipran or pharmaceutically acceptable salts thereof and hydrophobic release controlling agent which has substantially similar bioavailability under fed condition to that of commercially available Milnacipran hydrochloride (Savella®) Tablets administered twice daily.

DETAILED DESCRIPTION OF THE INVENTION

Figure 1:
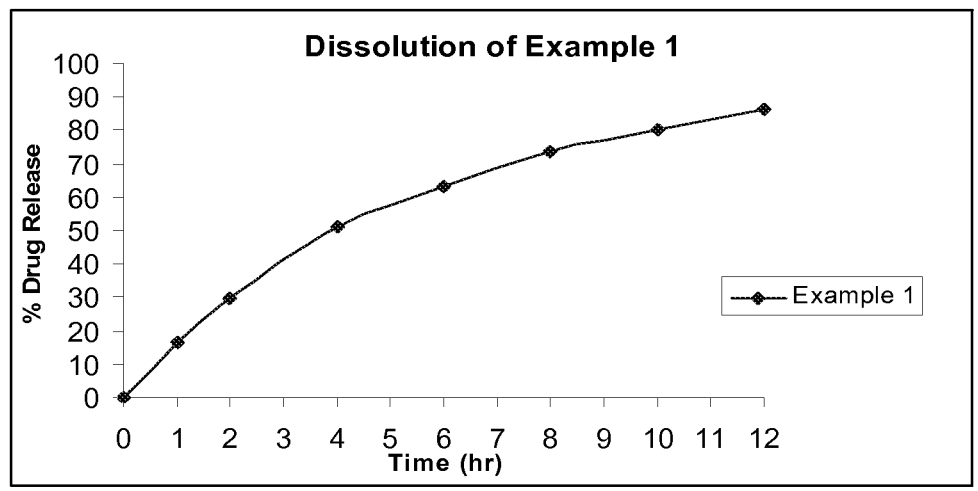
FIG. 1 shows a release profile of controlled release dosage forms of Milnacipran HCl of example 1, in 900 ml 0.1N HCl, USP apparatus Type I (Basket) at 100 rpm for 2 hrs followed by 900 ml Phosphate buffer pH 6.8 USP apparatus Type I (Basket) at 100 rpm.

The present invention is directed to novel controlled release pharmaceutical compositions comprising Milnacipran or pharmaceutically acceptable salts thereof, which provides complete dissolution between 8 to 20 hrs or the pharmaceutical composition of the present invention can be suitably designed to provide controlled release compositions that control release of the active over prolonged periods of time, at least for, 12 hours after oral administration.

As used herein "Milnacipran" also encompasses pharmaceutically acceptable, pharmacologically active derivatives of Milnacipran including both individual enantiomers of Milnacipran (dextrogyral and levrogyral enantiomers) and their pharmaceutically acceptable salts, mixtures of Milnacipran enantiomers and their pharmaceutically acceptable salts, and active metabolites of Milnacipran and their pharmaceutically acceptable salts, unless otherwise noted.

As used herein, "pharmaceutically acceptable salts" refer to derivatives of Milnacipran wherein the Milnacipran is modified by making acid-addition or base-addition salts thereof Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, methanesulfonic, ethane disulfonic, oxalic, isethionic and the like. The most preferable salt is hydrochloric salt.

The amount of Milnacipran or pharmaceutically acceptable salts thereof to be used in present invention ranges from about 25 to about 500 mg.

The term "controlled release compositions" herein refers to any composition or dosage form which comprises an active drug and which is formulated to provide a longer duration of pharmacological response after administration of the dosage form than is ordinarily experienced after administration of a corresponding immediate release composition comprising the same drug in the same amount. Controlled release compositions include, inter alia, those compositions described elsewhere as "extended release", "sustained release", "prolonged release", "programmed release", "time release" and/ or "rate controlled" compositions or dosage forms.

The controlled release pharmaceutical compositions of the present invention are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, glidants, dissolution enhancing agents and rate controlling agents.

The rate-controlling agent(s) used in admixture with the active ingredient may be selected from the group comprising hydrophilic release controlling agents, hydrophobic release controlling agents, and mixtures thereof. More preferably are the hydrophobic release controlling agents.

The hydrophilic release controlling agents are selected from but are not limited to hydroxypropyl methyl cellulose (HPMC), hydroxypropyl cellulose (HPC), hydroxyethyl cellulose (HEC) polyethylene oxide, polyvinyl alcohol, polyvinylpyrrolidone, xanthan gum, guar gum, chitosan and its derivatives, carbomer, carrageenan, carboxymethyl cellulose, sodium alginate, polyglycolized glycerides, polyethylenglycol, or mixture thereof.

The hydrophobic release controlling agents are selected from but are not limited to polyvinyl acetate dispersion, ethyl cellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), waxes such as beeswax, carnauba wax, paraffin wax, microcrystalline wax, and. ozokerite; fatty alcohols such as cetostearyl alcohol, stearyl alcohol, cetyl alcohol and myristyl alcohol, and fatty acid esters such as glyceryl monostearate; glycerol monooleate, acetylated monoglycerides, tristearin, tripalmitin, cetyl esters wax, glyceryl palmitostearate, glyceryl behenate, and hydrogenated vegetable oils.

The amount of the rate-controlling agent that may be used in the composition of the present invention is in the range from about 1% to about 80% by weight of the composition, Pereferably from about 1% to about 70% by weight of the composition and more preferebely from about 1% to about 60% by weight of the composition.

Diluents may be, for example, any pharmaceutically acceptable, non-toxic diluent. Particular examples include lactose, dextrose, sucrose, maltose, microcrystalline cellulose, starch, calcium hydrogen phosphate, mannitol and the like.

Binders may be, for example, starch, sugars, gums, low molecular weight hydroxypropyl methylcellulose, hydroxypropyl cellulose, hydroxyethyl cellulose or the like.

Dissolution enhancing agents include pharmaceutically acceptable organic acids. Examples include but not limited to ascorbic acid, succinic acid, malonic acid, oxalic acid, tartaric acid, fumaric acid, adipic acid, glucono delta-lactone and malic acid.

Lubricants may be, for example, talc, magnesium stearate, calcium stearate, stearic acid, sodium stearyl fumarate, sodium benzoate or the like.

Glidants may be, for example, colloidal silicon dioxide, talc or the like.

The term "controlled release pharmaceutical compositions" includes a pharmaceutical composition that encompasses one or more individual units. The individual units may be in form of granules, pellets, minitablets or beads. Granules, pellets, minitablets or beads of the present invention can be filled into a capsule or can be compressed into a tablet.

In a more preferred embodiment of the invention individual units are tablet and more preferably unit is a bilayer tablet.

The bilayer tablet composition of the present invention comprises first layer comprising Milnacipran or pharmaceutically acceptable salts thereof and release controlling agent which comprises hydrophobic control releasing agent, optionally other carrier material and second layer comprises of other suitable carrier material and optionally Milnacipran or pharmaceutically acceptable salts thereof Further the bilayer tablet composition of the present invention comprises first layer comprising Milnacipran or pharmaceutically acceptable salts thereof and hydrogenated vegetable oil optionally other carrier material and second layer which comprises copolymer of methacrylic acid and methyl meth acrylate, other suitable carrier material and optionally Milnacipran or pharmaceutically acceptable salts thereof.

A typical example of the pharmaceutical composition of the invention is Pseudo-geometric Drug Delivery System which comprises a) first layer comprising effective amounts of the Milnacipran or salts thereof and hydrophobic control releasing agent, and optionally other carrier material having defined geometric form, b) a second layer or a support-platform comprises of other suitable carrier material and optionally Milnacipran or pharmaceutically acceptable salts thereof, wherein carrier material comprises methacrylate polymer (Eudragit L or S).

Thus Pseudo-geometric Drug Delivery System comprises two layers wherein support platform remains intact in stomach, therefore tablet structure remains intact and thus it controls or prevents burst effect in stomach, which prevents dose dumping. Thus the system provides less release of drug in stomach and reduces the adverse effect like nausea and vomiting.

Solid oral dosage forms of the present invention may be prepared by any conventional techniques for example dry granulation, direct compression, wet granulation, and extrusion-spheronization, melt granulation, compression coating. Melt granulation is the preferred technique.

In the preferred embodiment of the present invention bilayer tablet composition is prepared my melt granulation, wherein a first tablet layer composition is prepared by
  a) melting release controlling agent and dispersing Milnacipran or pharmaceutically acceptable salts thereof in it;
  b) cooling above melted mass to room temperature and passing solid mass through suitable seive to obtain granules
  c) lubricating the granules
and second layer composition is prepared by
  a) mixing hydrophobic release controlling agent and other suitable carrier material and optionally Milnacipran or pharmaceutically acceptable salts thereof
  b) granulating above mixture with purified water followed by drying the granules and seiving through a suitable seive
  c) lubricating the granules
introducing both the granules into a tablet press; compressing said tablet layer composition to form different tablet layer; compressing both tablet layer compositions to form a bilayer tablet.

For direct compression, the second tablet layer composition may be prepared by dry-mixing the constituent components, e.g. by means of a high-intensity mixer or a free-fall blender.

For production of the bilayer tablet according to the present invention, the first and second tablet layer compositions are compressed in a bilayer tablet press, e.g. a rotary press in the bilayer tableting mode.

The invention provides a once daily controlled-release pharmaceutical composition comprising Milnacipran or pharmaceutically acceptable salts thereof and hydrophobic release controlling agent which is bioavailable to commercially available Milnacipran hydrochloride (Savella®) Tablets administered twice daily. A study was carried out to compare the rate and extent of absorption of single dose of two test formulations (T1 and T2) of Milnacipran and single dose of Savella® 50 mg (containing Milnacipran HCl 50 mg) tablets b.i.d. (one tablet each 12 hourly), administered under fed conditions. The controlled release pharmaceutical composition of the invention exhibits mean C. in the range of about 50-2000 ng/ml and $AUC_{(0-t)}$ in the range of 1000-8000 ng/mL*h.

In order to further illustrate the present invention, the following examples are given:

EXAMPLE 1

| Sr. No. | Ingredients | % w/w |
| --- | --- | --- |
| | 1st Layer: Intragranular Part | |
| 1 | Milnacipran HCl | 10-60 |
| 2 | Sterotex NF (Hydrogenated vegetable oil) | 10-50 |
| 3 | Colloidal silicon dioxide | 3-20 |
| 4 | Magnesium stearate | 2-10 |
| | Total Weight of 1st Layer | 200-300 |
| | 2nd Layer | |
| 1 | Eudragit L100-55 | 10-30 |
| 2 | Lactose Monohydrate | 1-20 |
| 3 | PVP K 30 | 1-20 |
| 4 | Purified Water | QS |
| | Total Weight of 2nd Layer | 50-150 |
| | Total tablet weight | 200-500 |

Brief Manufacturing Procedure:

1st Layer:
1. Weigh all ingredients.
2. Melt Sterotex & disperse Milnacipran HCl to it.
3. Cool above melted mass to room temperature.
4. Pass solid mass through 18#.
5. Lubricate above granules with colloidal silicon dioxide and Magnesium Stearate.

2nd Layer:
1. Mix Lactose, Povidone K30 & Eudragit L100-55.
2. Granulate above with Purified Water.
3. Dry the granules and sift through 20#. Lubricate granules with Aerosil & Magnesium stearate.
4. Compress above blend as bilayer tablet using suitable compression machine.
5. Optionally coated with Water permeable methacrylate polymer or Ethyl cellulose & hydroxyl propyl methyl cellulose.(Water soluble or water insoluble polymer).

EXAMPLE 2

| Sr. No. | Ingredients | % w/w |
| --- | --- | --- |
| | 1st Layer: Intragranular Part | |
| 1 | Milnacipran HCl | 20-50 |
| 2 | Sterotex NF (Hydrogenated vegetable oil) | 10-50 |
| 3 | Polyethylene Glycol NF | 5-20 |
| 4 | Silicon Dioxide | 2-10 |
| 5 | Magnesium stearate | 2-5 |
| | Total Dry Weight/Unit: | 200-300 |
| | 2nd Layer | |
| 1 | Eudragit L100-55 | 15-30 |
| 2 | Lactose Monohydrate | 2-10 |
| 3 | PVP K 30 | 2-20 |
| 4 | Purified Water | QS |
| | Total tablet weight | 200-600 |

Brief manufacturing Procedure:

1st Layer:
1. Weigh all ingredients.
2. Melt Sterotex & Polyethylene Glycol, disperse Milnacipran HCl to it.
3. Cool above melted mass to room temperature.
4. Pass solid mass through 18#.
5. Lubricate above granules with colloidal silicon dioxide and Magnesium Stearate.

2nd Layer:
1. Mix Lactose, Povidone K30 & Eudragit L100-55.
2. Granulate above with Purified Water.
3. Dry the granules and sift through 20#. Lubricate granules with silicon dioxide & Magnesium stearate.
4. Compress above blend as bilayer tablet using suitable compression machine.
5. Optionally coated with suitable acrylate polymer or Ethyl cellulose & hydroxyl propyl methylcellulose.

EXAMPLE 3

| Sr. No. | Ingredients | % w/w |
| --- | --- | --- |
| | 1st Layer: Intragranular Part | |
| 1 | Milnacipran HCl | 20-50 |
| 2 | Sterotex NF (Hydrogenated vegetable oil) | 10-50 |
| 3 | Lactose | 5-20 |
| 4 | Colloidal silicon dioxide | 3-10 |
| 5 | Magnesium stearate | 3-5 |
| | Total Dry Weight/Unit: | 200-300 |
| | 2nd Layer | |
| 1 | Eudragit L100-55 | 15-40 |
| 2 | Lactose Monohydrate | 3-10 |
| 3 | PVP K 30 | 3-10 |
| 4 | Purified Water | QS |
| | Total tablet weight | 400-700 |

Brief Manufacturing Procedure:

1st Layer:
1. Weigh all ingredients.
2. Melt Sterotex and Lactose & disperse Milnacipran HCl to it.
3. Cool above melted mass to room temperature.
4. Pass solid mass through 18#.
5. Mix 40# Lactose & sized granules of above step.
6. Lubricate above granules with colloidal silicon dioxide and Magnesium Stearate.

2nd Layer:
1. Mix Lactose, Povidone K30 & Eudragit L100-55.
2. Granulate above with Purified Water.
3. Dry the granules and sift through 20#. Lubricate granules with Aerosil & Magnesium stearate.
4. Compress above blend as bilayer tablet using suitable compression machine.
5. Optionally coated with Eudragit RL/RS (Water permeable polymer) or Ethyl cellulose & hydroxyl propyl methyl cellulose.(Water soluble or water insoluble polymer).

EXAMPLE 4

| Sr. No. | Ingredients | % w/w |
|---|---|---|
| | 1st Layer: Intragranular Part | |
| 1 | Milnacipran HCl | 20-50 |
| 2 | Sterotex NF (Hydrogenated vegetable oil) | 10-50 |
| 3 | Lactose | 5-20 |
| 4 | Colloidal silicon dioxide | 3-10 |
| 5 | Magnesium stearate | 3-5 |
| | Total Dry Weight/Unit: | 400-600 |
| | 2nd Layer | |
| 1 | Eudragit L100-55 | 15-40 |
| 2 | Lactose Monohydrate | 3-30 |
| 3 | PVP K 30 | 3-10 |
| 4 | Purified Water | QS |
| | Total tablet weight | 800-1500 |

Brief Manufacturing Procedure:
1st Layer:
1. Weigh all ingredients.
2. Melt Sterotex and Lactose & disperse Milnacipran HCl to it.
3. Cool above melted mass to room temperature.
4. Pass solid mass through 18#.
5. Mix 40# Lactose & sized granules of above step.
6. Lubricate above granules with colloidal silicon dioxide and Magnesium Stearate.

2nd Layer:
1. Mix Lactose, Povidone K30 & Eudragit L100-55.
2. Granulate above with Purified Water.
3. Dry the granules and sift through 20#. Lubricate granules with Aerosil & Magnesium stearate.
4. Compress above blend as bilayer tablet using 12 to 13 mm round shape punch.
5. Optionally coated with Eudragit RL/RS (Water permeable polymer) or Ethyl cellulose & hydroxyl propyl methyl cellulose (Water soluble or water insoluble polymer).

Figure 2:
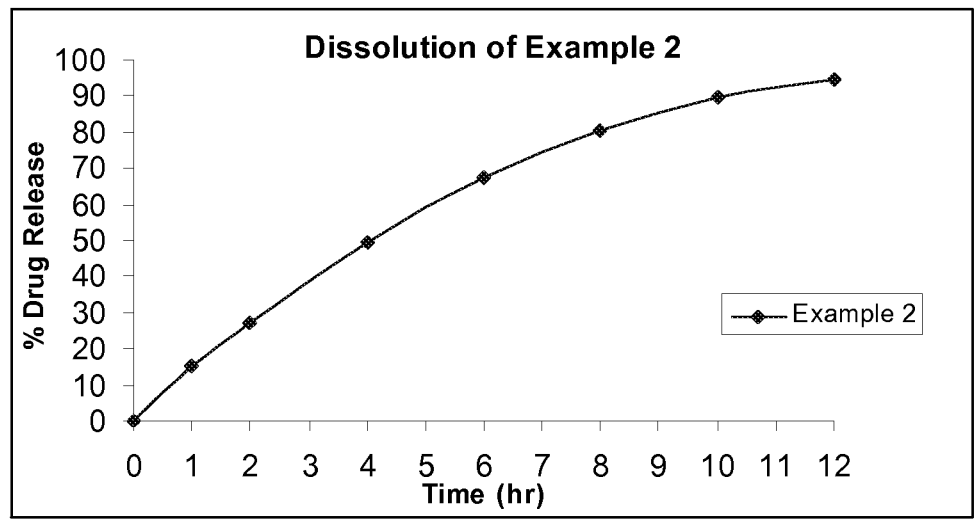
FIG. 2 shows a release profile of controlled release dosage forms of Milnacipran HCl of example 2, in 900 ml 0.1N HCl, USP apparatus Type I (Basket) at 100 rpm for 2 hrs followed by 900 ml Phosphate buffer pH 6.8 USP apparatus Type I (Basket) at 100 rpm.
Figure 3:
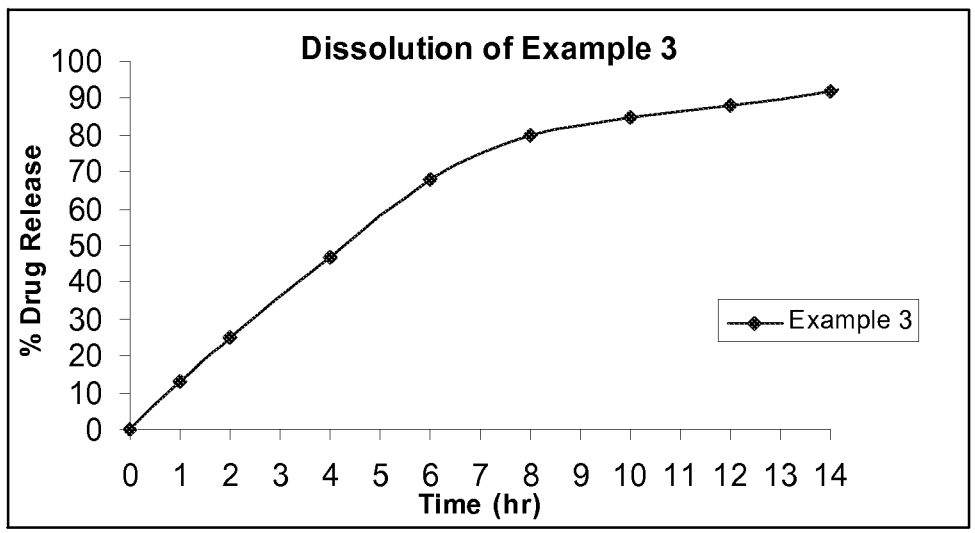
FIG. 3 shows a release profile of controlled release dosage forms of Milnacipran HCl of example 3, in 900 ml 0.1N HCl, USP apparatus Type I (Basket) at 100 rpm for 2 hrs followed by 900 ml Phosphate buffer pH 6.8 USP apparatus Type I (Basket) at 100 rpm.
Figure 4:
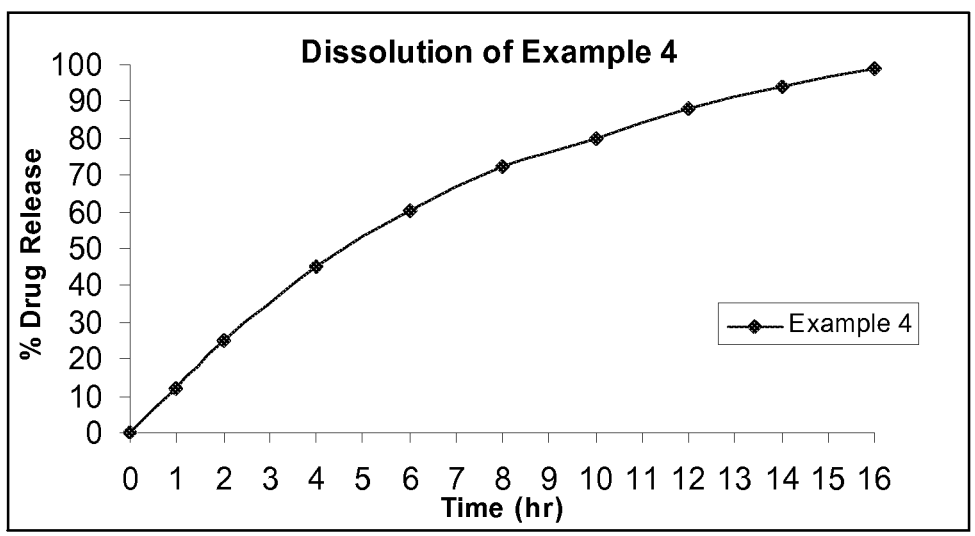
FIG. 4 shows a release profile of controlled release dosage forms of Milnacipran HCl of example 4, in 900 ml 0.1N HCl, USP apparatus Type I (Basket) at 100 rpm for 2 hrs followed by 900 ml Phosphate buffer pH 6.8 USP apparatus Type I (Basket) at 100 rpm.
Figure 5:
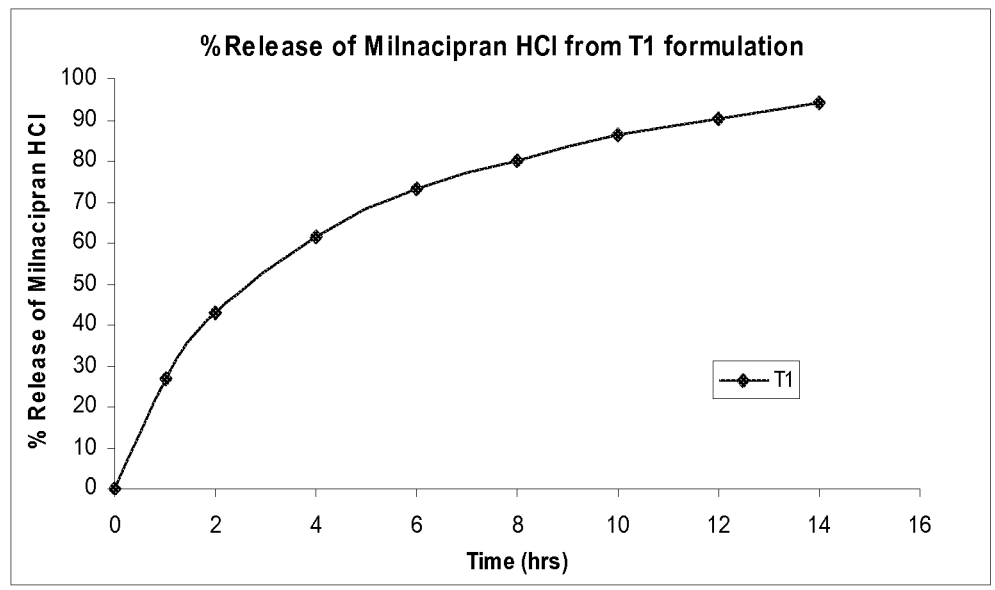
FIG. 5 shows a release profile of controlled release dosage forms of Milnacipran HCl of example T1, in 900 ml 0.1N HCl, USP apparatus Type I (Basket) at 100 rpm for 2 hrs followed by 900 ml Phosphate buffer pH 6.8 USP apparatus Type I (Basket) at 100 rpm.
Figure 6:
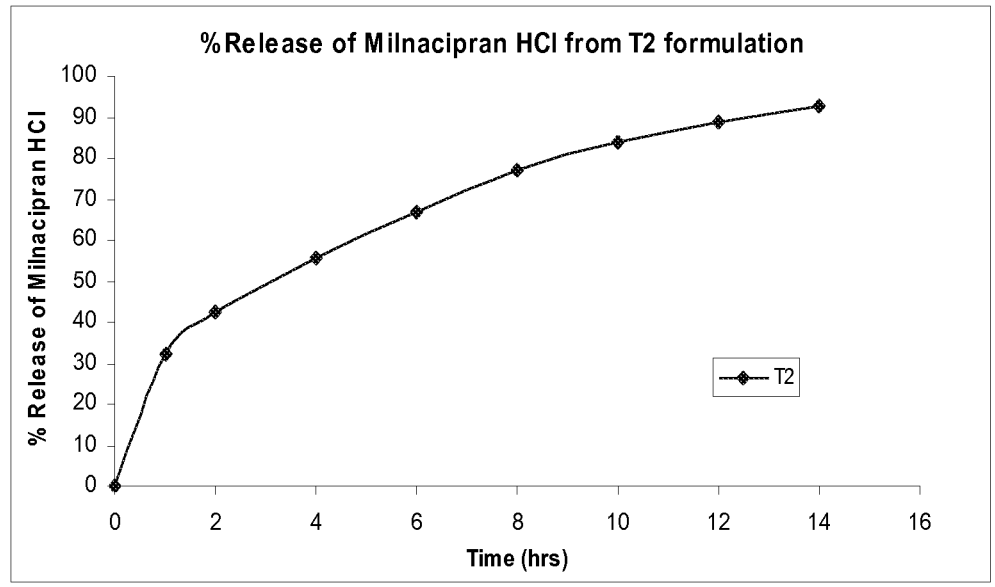
FIG. 6 shows a release profile of controlled release dosage forms of Milnacipran HCl of example T2 in 900 ml 0.1N HCl, USP apparatus Type I (Basket) at 100 rpm.
Figure 7:
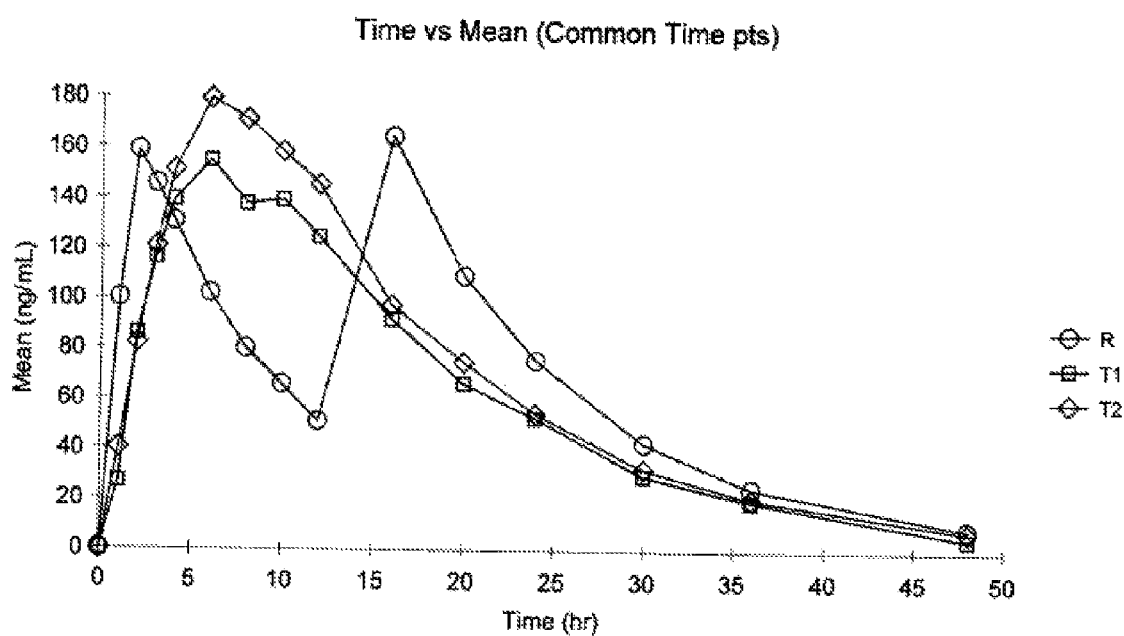
FIG. 7: Comparative plasma concentration against time for Savella™ (Milnacipran HCl) Tablets 50 mg (b.i.d.) vs. once daily Milnacipran Controlled Release Tablets 100 mg as Test Products ($T_1$ & $T_2$).

The results of in-vitro dissolution of pharmaceutical compositions of examples 1-4 are shown in FIG. 1-4 respectively.

Pharmacokinetic Studies

An open label, balanced, randomized, three-treatment, three-sequence, three-period, single dose, crossover relative bioavailability study was performed in 12 healthy, adult, male, human volunteers who meet all inclusion under standard fed conditions. The objective of the study was to compare the rate and extent of absorption of single dose of two formulations (T1 and T2) of Milnacipran and single dose of Savella® 50 mg (containing Milnacipran HCl 50 mg) tablets b.i.d. (one tablet each 12 hourly), administered under fed conditions in healthy, adult, male, human subjects in a randomized cross over study and also to improve adverse events like nausea and vomiting. To avoid vomiting/nausea effects due to investigational products, all subjects will also be administered with single dose of Granisetron HCl-1 mg tablet b.i.d. with sufficient quantity of water as required by subject (not more than 100 mL) as per following schedule:

Subjects Receiving Test (T1 or T2) Product: One tablet at 1 hour before dosing in the morning (i.e. at −1 hour of dosing) and one tablet at "11" hours post dose in the evening.

Subjects Receiving Reference (R) Product: One tablet at 1 hour before first dosing in the morning (i.e., at −1 hour of dosing) and one tablet at 1 hour before second dosing in the evening (i.e., at 11 hours).

Sampling Schedule:

A total of 19 blood samples were collected from each subject during each period at 1.00, 2.00, 3.00, 4.00, 4.50, 5.00, 5.50, 6.00, 7.00, 8.00, 10.00, 12.00, 16.00, 20.00, 24.00, 30.00, 36.00 and 48.00 hours post dose for reference as well as test product.

Washout Period:

A washout of at least 7 days was kept from the completion of dosing between two consecutive periods.

Following Pharmacokinetic Parameters of Test & Reference Products Were Compared:

Primary parameters: $C_{max}$, $AUC_{(0-t)}$ and $AUC_{(0-inf)}$

Results of Relative Bioavailability Assessment:

TABLE 1

Compilation of Pilot Bio Results of T1 Formulation:

| Test Parameters Mean | Reference | Test (T1) | % Relative Bioavailability |
|---|---|---|---|
| $C_{max}$ | 203.62 (142-280) | 192.40 (144-253) | 94.48 |
| $AUC_{(0-t)}$ | 3332.71 (2026-4709) | 2966.54 (1965-4174) | 89.01 |
| $AUC_{(0-inf)}$ | 3467.38 (2198-4913) | 3079.99 (2073-4280) | 88.82 |

TABLE 2

Compilation of Pilot Bio Results of T2 Formulation:

| Test Parameters Mean | Reference | Test (T2) | % Relative Bioavailability |
|---|---|---|---|
| $C_{max}$ | 203.62 (142-280) | 205.39 (153-329) | 100.86 |
| $AUC_{(0-t)}$ | 3332.71 (2026-4709) | 3322.38 (2130-4063) | 99.69 |
| $AUC_{(0-inf)}$ | 3467.38 (2198-4913) | 3439.87 (2205-4188) | 99.20 |

$C_{max}$ = Maximum plasma concentration
$AUC_{(0-t)}$ = Area under the plasma concentration vs. time curve from 0 hours to the time of last sample collected
$AUC_{(0-\infty)}$ = Area under the plasma concentration vs. time curve from 0 hours to infinity Test Formulation (T1)

| Sr. No. | Ingredients | Quantity Mg/Tablet |
|---|---|---|
| I | First Layer (Active Layer) | |
| 1 | Milnacipran HCl | 100.00 |
| 2 | Sterotex (Hydrogenated Vegetable Oil) | 100.00 |
| 3 | Colloidal Anhydrous Silica (Aerosil 200) | 7.00 |
| 4 | Magnesium Stearate | 3.00 |
| | Average Weight of First Layer | 210.00 |
| II | Second Layer (Inactive Layer) | |
| 1 | Eudragit L 100 | 51.00 |
| 2 | Lactose Monohydrate | 16.00 |
| 3 | Povidone K 30 | 8 |
| 4 | Purified Water | Q.S. |
| | Average Weight of Second Layer | 75.00 |
| | Average Weight of Uncoated Tablet | 285.00 |
| III | Color Coating | |
| 1 | Opadry Yellow | 5.00 |
| 2 | Isopropyl Alcohol | q.s. |
| 3 | Dichloromethane | q.s. |
| | Average Weight of Film Coated Tablet | 290.00 |

Brief Manufacturing Procedure:
A. Preparation of Active Layer:
1. Weigh all ingredients.
2. Pass Milnacipran HCl & Sterotex through 40# mesh. Melt Sterotex and disperse Milnacipran HCl in this melted mass with continuous stirring. Cool the mass to room temperature.
3. Pass the solid mass through 20#. Lubricate above granules with Aerosil and Magnesium Stearate.
B. Preparation of Inactive Layer:
1. Pass Lactose Monohydrate, Povidone K-30 & Eudragit L100 through 40#. Mix properly all ingredients.
2. Granulate this blend with Purified water. Dry granules & pass dried granules through 20#.
3. Pass Aerosil & Magnesium Stearate through 60# mesh and lubricate with above 20# passed granules.
C. Compression:
Compress above blends ($I^{st}$ & $II^{nd}$ Layer) using 9.6 mm round shape, bevelled edge punches plain on both side.
D. Film Coating of Tablets
Dissolve Opadry Yellow in Isopropyl alcohol & Dichloromethane mixture. Coat the tablets of step C using Opadry Yellow solution in a suitable coating machine till the desired weight gain is achieved. Cure the coated tablets for sufficient time in coating pan.
Test Formulation (T2)

| Sr. No. | Ingredients | Quantity Mg/Tablet |
| --- | --- | --- |
| I | First Layer (Active Layer) | |
| 1 | Milnacipran HCl | 100.00 |
| 2 | Sterotex (Hydrogenated Vegetable Oil) | 150.00 |
| 3 | Polyethylene glycol 4000 | 40.00 |
| 4 | Lactose Monohydrate | 340.00 |
| 5 | Mannitol (Pearlitol SD 200) | 60.00 |
| 6 | Colloidal Anhydrous Silica (Aerosil 200) | 7.00 |
| 7 | Magnesium Stearate NF | 3.00 |
| | Average Weight of First Layer | 700.00 |
| II | Second Layer (Inactive Layer) | |
| 1 | Eudragit L 100 | 50.00 |
| 2 | Lactose Monohydrate | 120.00 |
| 3 | Povidone K90 | 8.00 |
| 4 | Dicalcium Phosphate Anhydrous | 82.00 |
| 5 | Sterotex (Hydrogenated Vegetable Oil) | 30.00 |
| 6 | Colloidal Anhydrous Silica (Aerosil 200) | 6.00 |
| 7 | Magnesium Stearate | 4.00 |
| 8 | Purified Water | Q.S. |
| | Average Weight of Second Layer | 300.00 |
| | Average Weight of Core Tablet | 1000.00 |
| III | Color Coating | |
| 1 | Opadry Yellow | 20.00 |
| 2 | Isopropyl Alcohol | q.s. |
| 3 | Dichloromethane | q.s. |
| | Average Weight of Film Coated Tablet | 1020.00 |

Brief Manufacturing Procedure:
A. Preparation of Active Layer:
1. Weigh all ingredients.
2. Pass Milnacipran HCl, Polyethylene Glycol 4000, Sterotex (Hydrogenated Vegetable Oil) and Lactose monohydrate through 40# mesh.
3. Melt Polyethylene Glycol 4000 and Sterotex and disperse Milnacipran HCl in this melted mass with continuous stirring, then add DCL-11 (Lactose monohydrate) to it.
4. Cool the melted mass to room temperature. Pass the solid mass through 20# and add Mannitol extra granularly to it. Lubricate above granules with Aerosil and Magnesium Stearate.

B. Preparation of Inactive Layer:
1. Pass DCL-11, Povidone K-90, Eudragit L100, DCP (A Tab) & Sterotex through 40#. Mix properly all ingredients.
2. Granulate the blend with purified water. Dry granules & pass sized granules through 20#.
3. Pass Aerosil & Magnesium Stearate through 60# mesh and lubricate 20# passed granules.
C. Compression:
Compress above blends ($I^{st}$ & $II^{nd}$ Layer) using 13.3 mm round shape, bevelled edge punches plain on both side.
D. Film Coating of Tablets:
Dissolve Opadry Yellow in Isopropyl alcohol & Dichloromethane mixture. Coat the tablets using Opadry Yellow solution in a suitable coating machine till the desired weight gain is achieved. Cure the coated tablets for sufficient time in coating pan.

The invention claimed is:

1. A controlled release pharmaceutical composition comprising:
   a) a first layer consisting of an effective amount of the Milnacipran or pharmaceutically acceptable salt thereof, hydrogenated vegetable oil, and an optional pharmaceutically acceptable carrier,
   b) a second layer consisting of a hydrophobic release controlling agent selected from the group consisting of cellulose acetate phthalate, cellulose triacetate, poly(methyl methacrylate), poly(ethyl methacrylate), poly (butyl methacrylate), poly(isobutyl methacrylate), and poly(hexyl methacrylate), poly(isodecyl methacrylate), poly(lauryl methacrylate), poly(phenyl methacrylate), poly(methyl acrylate), poly(isoprooyl acrylate), poly9isobutyl acrylate), poly(octadecyl acrylate), or hydrogenated vegetable oil and, optionally, Milnacipran or a pharmaceutically acceptable salt thereof;
   wherein the controlled release pharmaceutical composition does not exhibit lag time when dissolution is carried out in 900 ml 0.1N HCl, USP apparatus Type I (Basket) at 100 rpm for 2 hrs, followed by 900 ml Phosphate buffer pH 6.8 USP apparatus Type I (Basket) at 100rpm.

2. The controlled release pharmaceutical composition of claim 1 wherein the amount of Milnacipran or pharmaceutically acceptable salts thereof ranges from about 25 mg to about 500 mg.

3. The controlled release pharmaceutical composition of claim 1 wherein the composition releases 90% of the total amount of Milnacipran or pharmaceutically acceptable salts thereof between 8 to 20 hours.

4. The controlled release pharmaceutical composition of claim 3 wherein the composition releases 90% of the total amount of Milnacipran or pharmaceutically acceptable salts thereof between 8 to 12 hours.

5. The controlled release pharmaceutical composition of claim 3 wherein the composition releases 90% of the total amount of Milnacipran or pharmaceutically acceptable salts thereof between 12 to 14 hours.

6. A once daily controlled release pharmaceutical composition comprising:
   a) a first layer consisting of an effective amount of the Milnacipran or a pharmaceutically acceptable salt thereof, hydrogenated vegetable oil, and an optional pharmaceutically acceptable carrier,
   b) a second layer consisting of a hydrophobic release controlling agent selected from the group consisting of cellulose acetate phthalate, cellulose triacetate, poly(methyl methacrylate), poly(ethyl methacrylate), poly (butyl methacrylate), poly(isobutyl methacrylate), and poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), or hydrogenated vegetable oil and, optionally, Milnacipran or a pharmaceutically acceptable salt thereof;

wherein the controlled release pharmaceutically composition has substantially similar bioavailability under fed condition to that of commercially available Milnacipran hydrochloride (Savella®) Tablets administered twice daily.

7. The controlled release pharmaceutical composition of claim 6, wherein the composition exhibits a mean $C_{max}$ from about 50 to about 2000 ng/ml.

8. The controlled release pharmaceutical composition of claim 7 wherein the composition exhibits a mean $C_{max}$ from about 50 to about 500 ng/ml.

9. The controlled release pharmaceutical composition of claim 6 wherein the composition exhibits a mean $AUC_{(0-t)}$ from about 1000 to about 8000 ng/mL*h.

10. The controlled release pharmaceutical composition of claim 9 wherein the composition exhibits a mean $AUC_{(0-t)}$ from about 1500 to about 5000 ng/mL*h.

11. The process of preparing a controlled release pharmaceutical composition of claim 1 comprises a) preparing a first layer consisting of i) melting hydrogenated vegetable oil and dispersing Milnacipran or pharmaceutically acceptable salts thereof in it; ii) cooling followed by sieving the melted mass to obtain granules; and iii) lubricating the granules, b) preparing a second layer consisting of granules which comprises hydrophobic release controlling agent selected from the group consisting of cellulose acetate phthalate, cellulose triacetate, poly(methyl methacrylate), poly(ethyl methacrylate), poly(butyl methacrylate), poly(isobutyl methacrylate), and poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), or hydrogenated vegetable oil and optionally Milnacipran or pharmaceutically acceptable salts thereof.

12. The controlled release pharmaceutical composition of claim 6, for the treatment of fibromyalgia.

* * * * *